United States Patent [19]

Uenobe et al.

[11] Patent Number: 4,489,067

[45] Date of Patent: Dec. 18, 1984

[54] LIPID REDUCING AGENTS

[75] Inventors: Fukuji Uenobe, Toyonaka; Shin Matsuura, Gifu; Nobuhiro Yamamoto, Sakai; Masakazu Shioyama, Hirakata, all of Japan

[73] Assignee: Yushiro Chemical Industry Co., Ltd., Osaka, Japan

[21] Appl. No.: 333,865

[22] Filed: Dec. 16, 1981

[30] Foreign Application Priority Data

Apr. 21, 1980 [JP] Japan ................................. 55-051613

[51] Int. Cl.$^3$ ............................................. A61K 35/78
[52] U.S. Cl. ...................................................... 424/195
[58] Field of Search ......................................... 424/195

[56] References Cited

FOREIGN PATENT DOCUMENTS 31-7518  8/1956  Japan .

Primary Examiner—Stanley J. Friedman
Assistant Examiner—John W. Rollins, Jr.
Attorney, Agent, or Firm—Birch, Stewart, Kolasch & Birch

[57] ABSTRACT

Substances which reduce the amount of lipids in serum and the liver are extracted from Yucca plants. These substances are capable of lowering high cholesterol and triglyceride values in serum as well as those in the livers of mammals and birds. A toxicity test in which these substances were administered to rats revealed that they have no acute toxicity.

16 Claims, No Drawings

LIPID REDUCING AGENTS

BACKGROUND AND FIELD OF THE INVENTION

The present invention relates to lipid reducing agents and more specifically to those agents which reduce the amount of lipids in serum and in the liver, said agents comprising substances solvent-extracted from Yucca plants.

Diseases caused by the accumulation of lipids in serum and in the liver have become a serious concern in recent years, and drugs which can alleviate these diseases have been much desired.

DISCLOSURE OF THE INVENTION

As a result of extensive research in connection with attempts to collect from Yucca plants substances which can reduce the amount of lipids in serum and in the liver, the inventors have attained the present invention.

According to the present invention, substances having a function of reducing the amount of lipids in serum and in the liver can be separated from Yucca plants and refined by the following two exemplary methods.

(1) The stems and rootstocks of Yucca plants are dried and powdered. The powder is then dissolved in a lower dialkyl ether such as ethyl ether to remove an ether-soluble portion and the residue is extracted with a lower alcohol. From the extract, the lower alcohol is distilled off and the residue is dried. This residue is used as an effective component and thus "lipid reducing agent I" is prepared.

(2) The stems and rootstocks of Yucca plants are dried and powdered. The powder is dissolved in a lower dialkyl ether such as ethyl ether to remove an ether-soluble portion. The residue is extracted with a lower alcohol and the extract is concentrated to obtain an extract. The extract is again extracted with water-saturated ethyl acetate and, from the extract, the water-saturated ethyl acetate is distilled off. The remaining fluid is adsorbed on silica gel and the adsorbed substances are eluted from the silica gel in two steps, namely in the first step using a mixed organic solvent consisting of a major proportion, e.g., eight volume parts of chloroform and a minor proportion, e.g., one volume part of a lower alcohol such as methyl alcohol and in the second step using a mixed organic solvent consisting of a major proportion, e.g., four volume parts of chloroform and a minor porportion, e.g., one volume part of a lower alcohol such as methyl alcohol. From the second eluate, the solvent is distilled off and the residue is dried. This residue is used as an effective component and thus "lipid reducing agent II" is prepared.

In the present invention, a lower alcohol such as methyl alcohol, ethyl alcohol or isopropyl alcohol can be used for extraction purposes.

The following examples are given merely as illustrative of the present invention and are not to be considered as limiting. Unless otherwise noted, all percentages therein and throughout the application are by weight.

EXAMPLE 1

Preparation of lipid reducing agent I

Stems and rootstocks of Yucca mohavensia were dried and powdered. One kilogram of the powder was dipped in 4 liters of ethyl ether for about 2 hours at room temperature. The resultant ethyl ether extract was removed. Then, to the ether-insoluble portion was added 4 liters of methyl alcohol. The mixture was refluxed with heating for 3 hours for extraction and then filtered after cooling. To the insoluble portion was added an additional 3.5 liters of methyl alcohol and a similar procedure was repeated. The two extracts were mixed and concentrated under reduced pressure to remove the methyl alcohol, and about 400 ml of a concentrated fluid was obtained. By drying the fluid, 324 g of a dried substance was obtained.

EXAMPLE 2

Preparation of lipid reducing agent II

Stems and rootstocks of Yucca mohavensia were dried and powdered. One kilogram of the powder was dipped in 4 liters of ethyl ether for about 2 hours at room temperature. The resultant ether extract was removed. Then, to the remaining ether-insoluble portion was added 4 liters of methyl alcohol and the mixture was refluxed with heating for 3 hours for extraction. After cooling, the mixture was filtered. To the methyl alcohol-insoluble fraction was added an additional 3.5 liters of methyl alcohol and a similar procedure was repeated. The two extracts were mixed and concentrated under reduced pressure to remove the methyl alcohol, and about 400 ml of a concentrated fluid was obtained. To this fluid was added about 2 liters of water and, using about 10 liters of ethyl acetate, droplet counter-current distribution chromatography was employed and the ethyl acetate-soluble fractions were collected. The solvent was distilled off from the acetate-soluble fractions, and using 2 Kg of silica gel ("Wako gel C-200" produced by Wako Pure Chemical Industries, Ltd.) as an adsorbent, liquid chromatography was conducted. The first elution was effected by the use of a mixed solvent consisting of eight volume parts of chloroform and one volume part of methyl alcohol, and the eluate was discarded. The second elution was conducted using a mixed solvent comprising four volume parts of chloroform and one volume part of methyl alcohol. The solvent was distilled off from the eluate and 17 g of a dried solid substance was obtained.

Effects of lipid reducing agents I and II

The substance prepared by the above method (1), namely the lipid reducing agent I, has a remarkable effect in lowering high cholesterol values in serum and in the liver. Also, the substance prepared by the method (2), namely the lipid reducing agent II, is quite effective in lowering high cholesterol values and high triglyceride values in serum and in the liver.

The lipid reducing agents I and II prepared in accordance with the present invention can be applied to mammals such as man and cattle as well as to birds such as domestic fowl.

Animal tests showing the effects of the lipid reducing agents according to the present invention are illustrated hereunder.

TEST 1

Animal test for lipid reducing agent I

As test animals, 15 Wister male rats weighing an average of 151 grams were used. They were divided into the following three groups each consisting of five rats.

(A) Standard dietary group

These rats were nurtured using a standard diet of "Powdered Feed MF for Rats and Mice" manufactured by Oriental Yeast Industries, Ltd.

(B) Control group

These rats were nurtured using a high-cholesterol diet which was the above standard diet to which were added 1.0% of cholesterol and 0.2% of cholic acid.

(C) Test group

These rats were nurtured using a diet which was the above high-cholesterol diet to which was added 1.5% of the lipid reducing agent I obtained in Example 1.

The rats of the above three groups were raised for 15 days as noted above and the diet administration was terminated. Six hours later, they were killed by decapitation. The blood of each was collected separately and each serum was isolated. Also, a predetermined quantity of liver was taken out from each rat for use in the test.

For the determination of total cholesterol and free cholesterol in each serum there was used a reagent for cholesterol measurement manufactured by Wako Pure Chemical Industries, Ltd. (branded as "Cholesterol Test"). A reagent for triglyceride measurement manufactured by Wako Pure Chemical Industries, Ltd. (branded as "Triglyceride Test") was used for the determination of serum triglycerides. The determination of total cholesterol and free cholesterol in each liver was carried out in accordance with the Sperry-Webb method. The body weight of each rat was measured before and after its growth. The results of the cholesterol and triglyceride measurements are shown in Table 1 and the results of the body weight measurements are shown in Table 2.

TABLE 1

| | | Serum (mg/dl) | | | Liver (mg/100 g) | |
|---|---|---|---|---|---|---|
| | | Total cholesterol | Free cholesterol | Triglyceride | Total cholesterol | Free cholesterol |
| (B) | control group, 5 rats | 159.5 ± 13.9 (note 1) | 33.6 ± 3.6 | 105.8 ± 8.3 | 2422.8 ± 158.1 | 413.6 ± 11.0 |
| (C) | test group, 5 rats | 100.5 ± 10.7 | 24.7 ± 1.5 | 94.2 ± 8.4 | 1656.2 ± 148.0 | 344.5 ± 9.3 |
| P level (significant level) | | P <0.01 | P <0.05 | (note 2) | P <0.01 | P <0.05 |
| (A) | standard dietary group, 5 rats | 73.6 ± 4.7 | 9.2 ± 1.2 | 71.8 ± 10.5 | 242.6 ± 19.1 | 196.9 ± 13.7 |

Notes:
(1) Mean value ± standard error
(2) No significant difference observed

TABLE 2

| | | Days of growth | | |
|---|---|---|---|---|
| Group | | 0 day | 15 days | Judgment |
| (A) | standard dietary group | 150.8 ± 1.5 (note 3) | 281.8 ± 3.1 | No significant difference is |
| (B) | control group | 151.0 ± 1.1 | 279.4 ± 4.5 | observed among |
| (C) | test group | 151.0 ± 1.2 | 277.6 ± 5.1 | (A), (B) and (C) |

Note:
(3) Unit is in grams. Mean value ± standard error

It is apparent from the test results of Table 1 that the lipid reducing agent I according to the present invention reduced the lipid concentration which had been increased in the serum and livers to a strikingly significant difference, except for the triglyceride values in the serum. The test results of Table 2 indicate that the administration of the lipid reducing agent I did not give any effect on the body weight.

TEST 2

Animal test for lipid reducing agent II

As test animals, 15 Wister male rats weighing an average of 110 grams were used. They were divided into the following three groups each consisting of five rats.

(A) Standard dietary group

These rats, were raised with the same standard diet as that in Test 1.

(B) Control group

These rats were raised with the same high-cholesterol diet as that in Test 1.

(C) Test group

These rats were raised with said high-cholesterol diet to which was added 1.0% of the lipid reducing agent II according to the present invention.

The rats of the above three groups were tested in accordance with the same test methods and conditions as those set forth in Test 1. The results of the cholesterol and triglyceride measurements are shown in Table 3 and the results of the body weight measurements are shown in Table 4.

TABLE 3

| | | Serum (mg/dl) | | | Liver (mg/100 g) | |
|---|---|---|---|---|---|---|
| | | Total cholesterol | Free cholesterol | Triglyceride | Total cholesterol | Free cholesterol |
| (B) | control group, 5 rats | 154.3 ± 3.7 (note 4) | 23.2 ± 1.7 | 117.7 ± 6.4 | 1844.0 ± 21.0 | 547.6 ± 37.2 |
| (C) | test group, 5 rats | 97.5 ± 5.6 | 11.6 ± 1.7 | 65.6 ± 7.1 | 368.4 ± 42.2 | 272.6 ± 13.6 |
| P level (significant level) | | P <0.001 | P <0.005 | P <0.005 | P <0.001 | P <0.001 |
| (A) | standard | 85.0 ± 1.3 | 11.4 ± 0.6 | 76.0 ± 5.3 | 353.3 ± 48.8 | 281.0 ± 18.1 |

TABLE 3-continued

| | Serum (mg/dl) | | | Liver (mg/100 g) | |
|---|---|---|---|---|---|
| | Total cholesterol | Free cholesterol | Triglyceride | Total cholesterol | Free cholesterol |
| dietary group, 5 rats | | | | | |

Note:
(4) Mean value ± standard error

TABLE 4

| | | Days of growth | | |
|---|---|---|---|---|
| | Group | 0 day | 15 days | Judgment |
| (A) | standard dietary group | 108.5 ± 1.0 (note 5) | 191.8 ± 1.7 | No significant difference is observed among (A), (B) and (C) |
| (B) | control group | 108.2 ± 2.0 | 191.8 ± 7.9 | |
| (C) | test group | 108.0 ± 0.9 | 191.5 ± 2.1 | |

Note:
(5) Unit is in grams. Mean value ± standard error

Table 3 shows that the lipid reducing agent II according to the present invention was effective with a strikingly significant difference in reducing the lipid concentration which had been increased in the serum and livers. Also, Table 4 indicates that there was no effect on the body weight due to the administration of the lipid reducing agent II.

Administration Method and Toxicity

The lipid reducing agent I according to the present invention is suitably orally administered in an amount of about 0.8 to 2.0 g daily per 1 Kg of body weight. With respect to toxicity, in a test in which the lipid reducing agent I was orally administered to 20 rats in an amount of 10 g daily per 1 Kg of body weight and these rats were raised or grown for 30 days, no dead rats were observed and also no acute toxicity was recognized. Also, as described previously, no significant difference of body weight was observed between rats raised with the standard diet and rats raised with the diet containing the lipid reducing agent I.

The lipid reducing agent II according to the present invention may suitably be orally administered in an amount of about 0.5 to 1.0 g daily per 1 Kg of body weight. In a test in which the lipid reducing agent II was orally administered to 20 rats in the amount of 5 g daily per 1 Kg of body weight and these rats were raised for 30 days, no dead rats were observed and also no acute toxicity was recognized. Also, as described previously, no significant difference of body weight was observed between rats raised with the standard diet and rats raised with the diet containing the lipid reducing agent II.

From the above results, it can be seen that the lipid reducing agents according to the present invention can be used as drugs for reducing the amounts of cholesterol and triglycerides in the serum of mammals (including man) and birds and also as drugs for reducing the amounts of cholesterol and triglycerides in the livers thereof. Such lipid reducing agents can be employed as the active ingredient in conventional pharmaceutical preparations for oral administration, such as tablets, capsules, dragees and the like, comprising the active ingredient and at least one conventional pharmaceutically acceptable carrier or excipient.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An agent for reducing the amount of cholesterol in serum and in the liver which is obtained by drying and powdering the stems and rootstocks of *Yucca mohavensia*, dissolving the powder in a lower dialkyl ether, discarding the ether-soluble portion, extracting the ether-insoluble portion with a lower alcohol from the extract and drying the residue.

2. An agent in accordance with claim 1, wherein said lower dialkyl ether is diethyl ether.

3. An agent in accordance with claim 1, wherein said lower alcohol is a member selected from the group consisting of methyl alcohol, ethyl alcohol, and isopropyl alcohol.

4. An agent in accordance with claim 2, wherein said lower alcohol is methyl alcohol.

5. A pharmaceutical composition comprising as an active ingredient an effective amount of an agent according to any one of claims 1, 2 or 4, and at least one pharmaceutically acceptable carrier or excipient.

6. A method for reducing the amount of cholesterol in serum and in the liver which comprises orally administering to a human or animal an effective cholesterol reducing amount of an agent according to claim 1 or claim 2.

7. The method of claim 6, wherein a dosage of about 0.8 to 2.0 g of said agent per 1 kg of body weight is administered daily.

8. An agent for reducing the amount of cholesterol and triglycerides in serum and in the liver which is obtained by drying and powdering the stems and rootstocks of *Yucca mohavensia*, dissolving the powder in a lower dialkyl ether, discarding the ether-soluble portion, extracting the ether-insoluble portion with a lower alcohol, concentrating the extract, extracting said extract with water-saturated ethyl acetate, distilling off the water-saturated ethyl acetate from the extract, adsorbing the remaining fluid on silica gel, eluting with a first mixed solvent consisitng of a major proportion of chloroform and a minor proportion of methyl alcohol and then eluting with a second mixed solvent consisting of a major proportion of chloroform and a minor proportion of methyl alcohol, distilling off the solvent from the second eluate and drying the residue.

9. An agent in accordance with claim 8, wherein said lower dialkyl ether is diethyl ether.

10. An agent in accordance with claim 8, wherein said lower alcohol is a member selected from the group consisting of methyl alcohol, ethyl alcohol, and isopropyl alcohol.

11. An agent in accordance with claim 9, wherein said lower alcohol is methyl alcohol.

12. An agent in accordance with claim 8, wherein said first mixed solvent comprises a mixture of about eight volume parts of chloroform and one volume part of methyl alcohol and said second mixed solvent comprises a mixture of about four volume parts of chloroform and one volume part of methyl alcohol.

13. An agent in accordance with claim 9, wherein said lower alcohol is methyl alcohol and said first mixed solvent comprises a mixture of about eight volume parts of chloroform and one volume part of methyl alcohol and said second mixed solvent comprises a mixture of about four volume parts of chloroform and one volume part of methyl alcohol.

14. A pharmaceutical composition comprising as an active ingredient an effective amount of an agent according to any one of claims 8, 9 or 13, and at least one pharmaceutically acceptable carrier or excipient.

15. A method for reducing the amount of cholesterol and triglycerides in serum and in the liver which comprises orally administering to a human or animal an effective amount of an agent according to claim 8 or claim 13.

16. The method of claim 15, wherein a dosage of about 0.5 to 1.0 g of said agent per 1 kg of body weight is administered daily.

* * * * *